United States Patent
Swift et al.

(10) Patent No.: US 12,263,104 B2
(45) Date of Patent: Apr. 1, 2025

(54) SELF EXPANDING STENTS AND METHODS

(71) Applicant: Cook Medical Technologies LLC, Bloomington, IN (US)

(72) Inventors: Richard A. Swift, South Bend, IN (US); Sam C. Mullins, Limerick (IE); Stephen T. Clancy, County Clare (IE)

(73) Assignee: Cook Medical Technologies LLC, Bloomington, IN (US)

( * ) Notice: Subject to any disclaimer, the term of this patent is extended or adjusted under 35 U.S.C. 154(b) by 9 days.

(21) Appl. No.: 17/750,042

(22) Filed: May 20, 2022

(65) Prior Publication Data

US 2023/0000648 A1  Jan. 5, 2023

Related U.S. Application Data

(63) Continuation-in-part of application No. 17/713,399, filed on Apr. 5, 2022, now Pat. No. 11,896,507.

(Continued)

(51) Int. Cl.
*A61F 2/915* (2013.01)

(52) U.S. Cl.
CPC .... *A61F 2/915* (2013.01); *A61F 2002/91541* (2013.01); *A61F 2002/91558* (2013.01);
(Continued)

(58) Field of Classification Search
CPC .. A61F 2/88; A61F 2/844; A61F 2/915; A61F 2230/0039; A61F 2230/0052; A61F 2250/0036; A61F 2250/0037; A61F 2250/001; A61F 2250/0067; A61F 2002/91541; A61F 2002/91558;
(Continued)

(56) References Cited

U.S. PATENT DOCUMENTS 6,231,598 B1   5/2001   Berry et al.
6,464,720 B2  10/2002   Boatman et al.
(Continued)

FOREIGN PATENT DOCUMENTS

EP   1236445 A2   9/2002
EP   1917931      5/2008
EP   3281668 A1   2/2018

OTHER PUBLICATIONS

International Application No. PCT/US2022/023012 International Search Report and Written Opinion, mailed Jun. 17, 2022.
(Continued)

*Primary Examiner* — Tan-Uyen T Ho
*Assistant Examiner* — Osama Nemer
(74) *Attorney, Agent, or Firm* — Woodard, Emhardt, Henry, Reeves & Wagner, LLP

(57) ABSTRACT

A stent comprises a framework that includes a sequence of cells that each occupy a discrete segment of the stent length, and each of the cells includes a plurality of struts with ends connected at respective vertices. In some forms the framework includes T-bars that connect adjacent cells, where the T-bars have a column that has a minimum width perpendicular to the long axis that is wider than a maximum width of each of the struts, and the column defines at least one slot. In other forms, the framework exhibits geometries that facilitate a high packing density for the framework when the stent is in a compressed tube or loading configuration.

25 Claims, 8 Drawing Sheets

Related U.S. Application Data

(60) Provisional application No. 63/313,902, filed on Feb. 25, 2022, provisional application No. 63/190,906, filed on May 20, 2021.

(52) U.S. Cl.
CPC ............... *A61F 2002/91583* (2013.01); *A61F 2230/0052* (2013.01); *A61F 2250/001* (2013.01)

(58) Field of Classification Search
CPC .. A61F 2002/91583; A61F 2002/91525; A61F 2002/91566
USPC .................................................. 623/1.34, 1.15
See application file for complete search history.

(56) References Cited

U.S. PATENT DOCUMENTS

| | | | |
|---|---|---|---|
| 6,558,415 B2 | 5/2003 | Thompson | |
| 6,827,732 B2 | 12/2004 | Thompson | |
| 7,381,217 B2 | 6/2008 | Tischler | |
| 8,740,968 B2* | 6/2014 | Kao | A61F 2/95 |
| | | | 623/1.16 |
| 9,381,103 B2 | 7/2016 | Abunassar | |
| 9,498,360 B2* | 11/2016 | Layman | A61F 2/89 |
| 9,827,120 B2* | 11/2017 | Gregorich | A61F 2/915 |
| 10,004,623 B2 | 6/2018 | Dom et al. | |
| 10,849,769 B2 | 12/2020 | Harrison et al. | |
| 11,628,077 B2 | 4/2023 | Ramzipoor et al. | |
| 2001/0027339 A1 | 10/2001 | Boatman et al. | |
| 2002/0120322 A1 | 8/2002 | Thompson et al. | |
| 2002/0123798 A1* | 9/2002 | Burgermeister | A61F 2/91 |
| | | | 623/1.17 |
| 2006/0025847 A1 | 2/2006 | Parker | |
| 2006/0271170 A1* | 11/2006 | Gale | A61F 2/915 |
| | | | 623/1.49 |
| 2008/0255655 A1 | 10/2008 | Kusleika et al. | |
| 2008/0294238 A1 | 11/2008 | Tischler et al. | |
| 2009/0204200 A1 | 8/2009 | Bales, Jr. et al. | |
| 2009/0240318 A1* | 9/2009 | Chalekian | A61F 2/856 |
| | | | 623/1.35 |
| 2010/0004735 A1 | 1/2010 | Yang et al. | |
| 2010/0114296 A1 | 5/2010 | Case et al. | |
| 2010/0292777 A1 | 11/2010 | Meyer et al. | |
| 2010/0292778 A1 | 11/2010 | Roeder et al. | |
| 2012/0215298 A1* | 8/2012 | Hansen | A61F 2/915 |
| | | | 623/1.13 |
| 2013/0073052 A1 | 3/2013 | Kim et al. | |
| 2013/0123905 A1* | 5/2013 | Abunassar | A61F 2/89 |
| | | | 623/1.16 |
| 2013/0197617 A1* | 8/2013 | Armstrong | A61F 2/90 |
| | | | 623/1.2 |
| 2016/0120671 A1 | 5/2016 | Higashi et al. | |
| 2018/0140444 A1* | 5/2018 | Neuss | A61F 2/915 |
| 2018/0360630 A1 | 12/2018 | Kim et al. | |
| 2021/0077283 A1* | 3/2021 | Yeh | A61F 2/86 |
| 2022/0370215 A1 | 11/2022 | Swift et al. | |

OTHER PUBLICATIONS

Non-Final Office Action dated Jul. 21, 2023 for U.S. Appl. No. 17/713,399, 33 pgs.

* cited by examiner

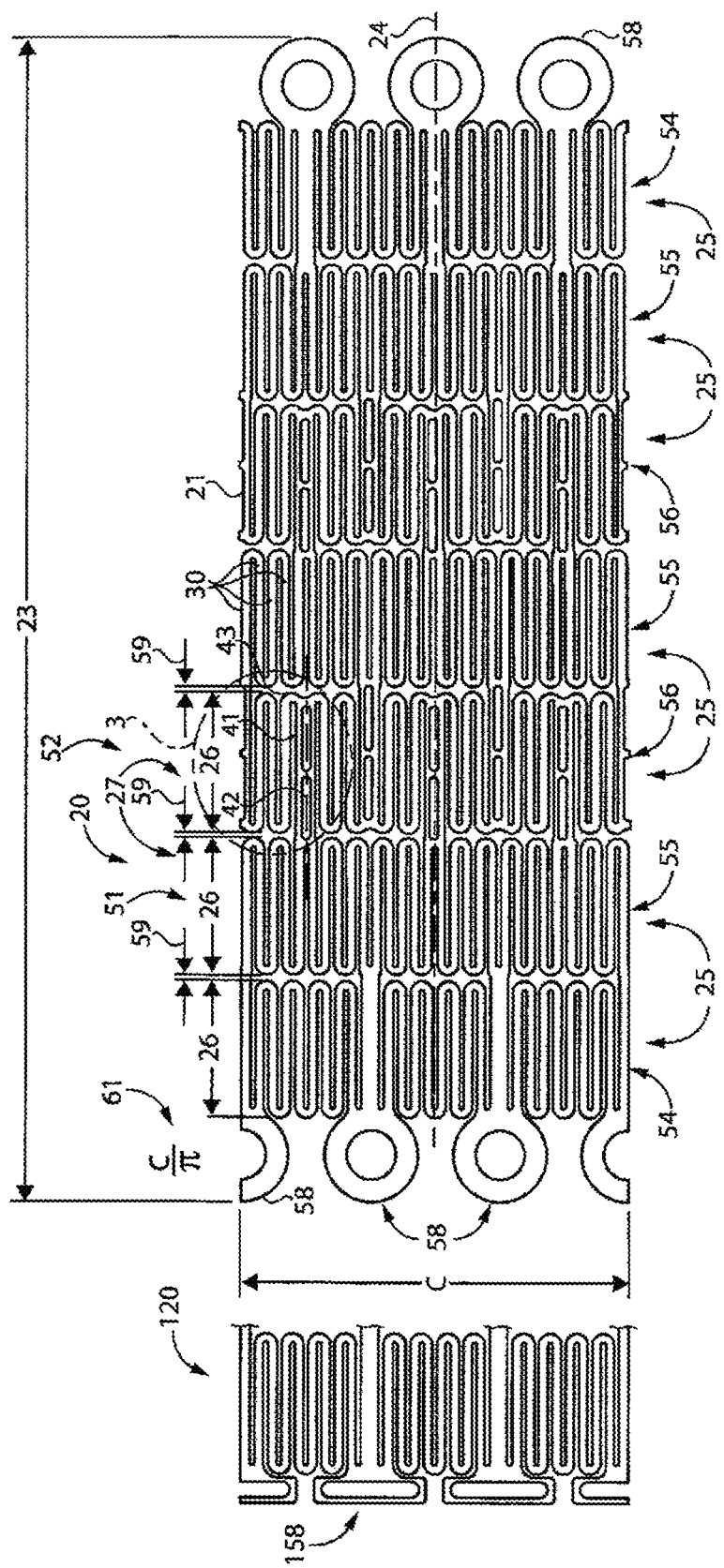

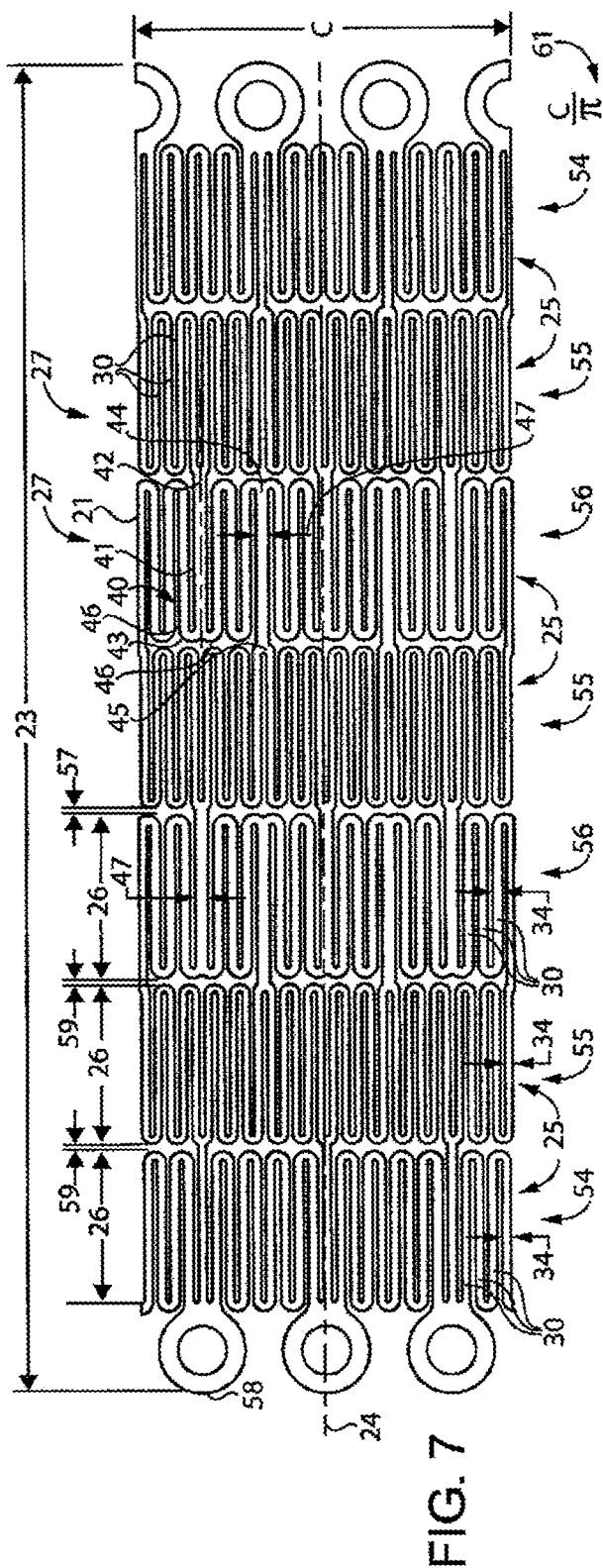
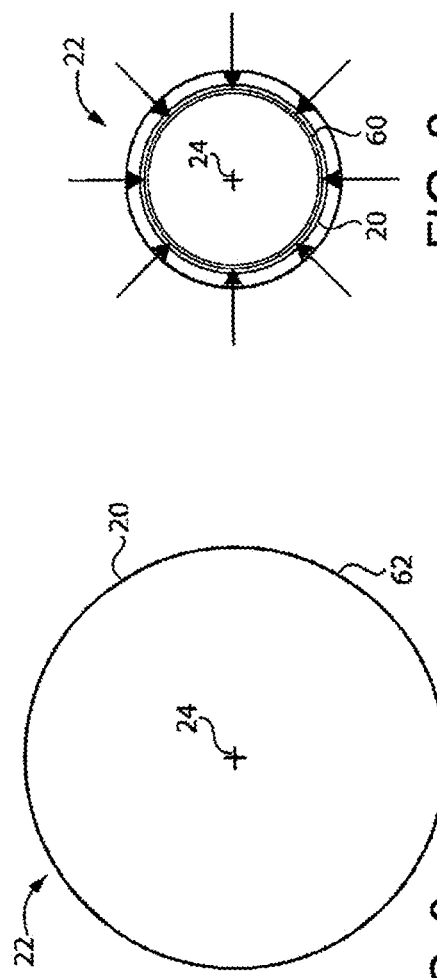
FIG. 7
FIG. 9
FIG. 8

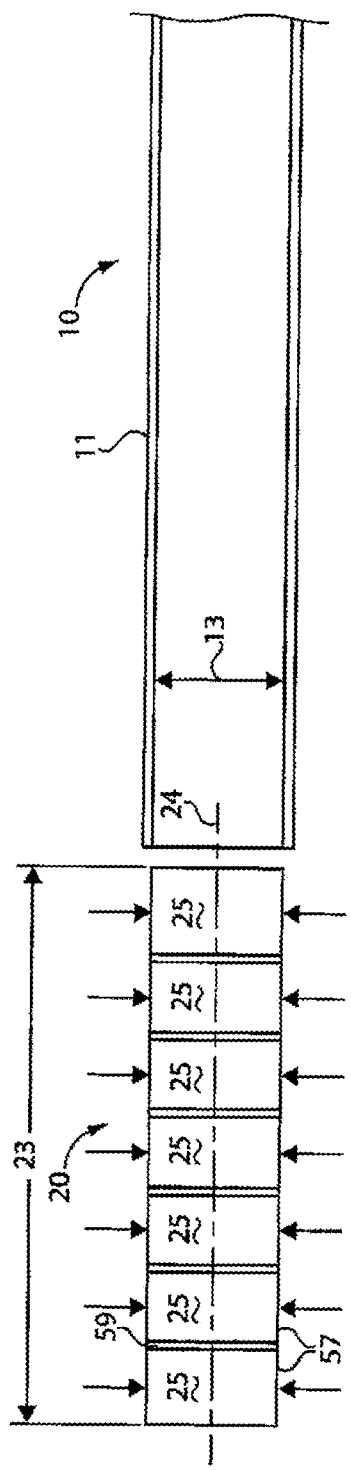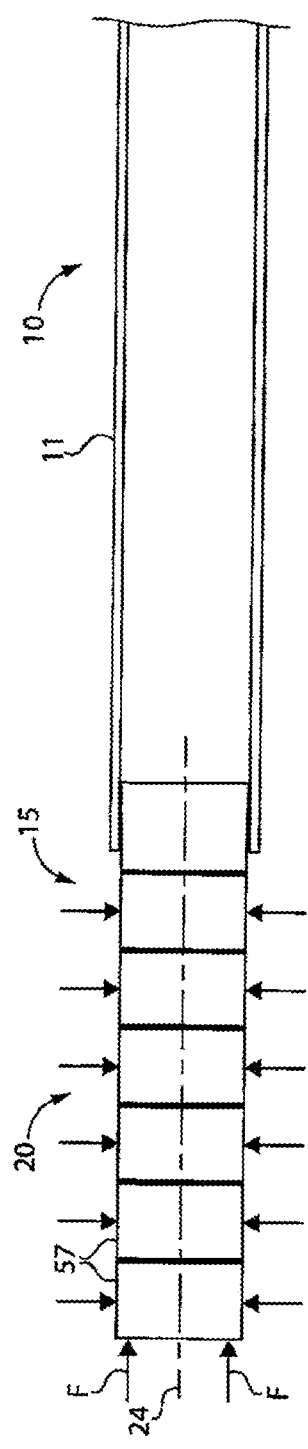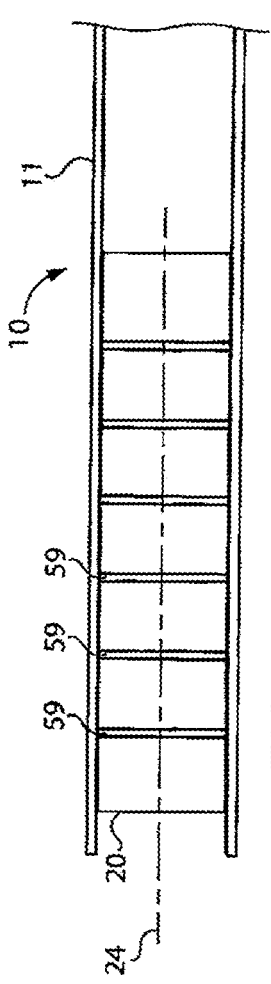

SELF EXPANDING STENTS AND METHODS

CROSS-REFERENCE TO RELATED APPLICATIONS

This application is a continuation-in-part of U.S. patent application Ser. No. 17/713,399 filed Apr. 5, 2022, which claims the benefit of U.S. Provisional Application No. 63/190,906, filed May 20, 2021, and this application claims the benefit of U.S. Provisional Application No. 63/313,902 filed Feb. 25, 2022, which are all incorporated herein by reference.

TECHNICAL FIELD

The present disclosure relates generally to stents, and more particularly in certain aspects to a stent structure that improves loadability into a stent delivery system.

BACKGROUND

The use of stents to treat various organs, such as the vascular system, colon, biliary tract, urinary tract, esophagus, trachea and the like, has become common in recent years. Stents are most commonly used to treat blockages, occlusions, narrowing ailments and other similar problems that restrict flow through a passageway. One area where stents are commonly used for treatment involves implanting an endovascular stent into the vascular system in order to improve or maintain blood flow through narrowed arteries. However, stents are also used in other treatments as well, such as the treatment of aneurysms. Stents have been shown to be useful in treating various vessels throughout the vascular system, including both coronary vessels and peripheral vessels (e.g., carotid, brachial, renal, iliac and femoral). In addition, stents have been used in other body vessels as well, such as the digestive tract.

The use of stents in coronary and peripheral vessels has drawn particular attention from the medical community because of the growing number of people each year that suffer from vasculature problems associated with stenosis (i.e., narrowing of a vessel). This has led to an increased demand for medical procedures to treat such problems. The widespread frequency of heart problems and other vasculature problems may be due to a number of societal changes, including the tendency of people to exercise less and the prevalence of unhealthy diets, in conjunction with the fact that people generally have longer life spans now than previous generations. Stents have become a popular alternative for treating vascular stenosis because stenting procedures are considerably less invasive than conventional procedures. For example, stenosis of the coronary arteries was traditionally treated with bypass surgery. In general, bypass surgery involves splitting the chest bone to open the chest cavity and grafting a replacement vessel onto the heart to bypass the blocked, or stenosed, artery. However, coronary bypass surgery is a very invasive procedure that is risky and requires a long recovery time for the patient. Vascular stents are also being more widely used to treat many different peripheral arteries due to the minimally invasive nature of stenting procedures. To address the growing demand for minimally invasive medical procedures for the treatment of coronary arteries, peripheral arteries and other passageway problems, the medical community has begun to turn away from conventional invasive procedures like bypass surgery and increasingly the treatment of choice now involves a variety of stenting procedures.

Many different types of stents and stenting procedures are possible. In general, however, stents are typically designed as tubular support structures that may be inserted percutaneously and transluminally through a body passageway. Traditionally, stents are made from a metal or other synthetic material with a series of radial openings extending through the support structure of the stent to facilitate compression and expansion of the stent. Although stents may be made from many types of materials, including non-metallic materials, common examples of metallic materials that may be used to make stents include stainless steel, nitinol, cobalt-chrome alloys, amorphous metals, tantalum, platinum, gold and titanium. Typically, stents are implanted within a passageway by positioning the stent within the area to be treated and then expanding the stent from a compressed diameter to an expanded diameter. The ability of the stent to expand from a compressed diameter makes it possible to thread the stent to the area to be treated through various narrow body passageways while the stent is in the compressed diameter. Once the stent has been positioned and expanded at the area to be treated, the tubular support structure of the stent contacts and radially supports the inner wall of the passageway. As a result, the implanted stent mechanically prevents the passageway from narrowing and keeps the passageway open to facilitate fluid flow through the passageway.

Stents can generally be characterized as either balloon-expandable or self-expanding. However, stent designs and implantation procedures vary widely. For example, although physicians often prefer particular types of stents for certain types of procedures, the uses for balloon-expandable and self-expanding stents sometimes overlap and procedures related to one type of stent may be adapted to other types of stents.

Self-expanding stents are increasingly used and accepted by physicians for treating a variety of ailments. Self-expanding stents are usually made of shape memory materials or other elastic materials that act like a spring. Typical metals used in this type of stent include nitinol and 304 stainless steel. A common procedure for implanting a self-expanding stent involves a two-step process. First, the narrowed vessel portion to be treated is dilated with a balloon but without a stent mounted on the balloon. Second, a stent is implanted into the dilated vessel portion. To facilitate stent implantation, the stent is installed on the end of a catheter in a compressed, small diameter state and is usually retained in the small diameter by inserting the stent into a sheath at the end of the catheter. The stent is then guided to the balloon-dilated portion and is released from the catheter by pulling the restraining sheath off the stent. Once released from the restraining sheath, the stent radially springs outward to an expanded diameter until the stent contacts and presses against the vessel wall. Traditionally, self-expanding stents have been more commonly used in peripheral vessels than in coronary vessels due to the shape memory characteristic of the metals that are used in these stents. One advantage of self-expanding stents for peripheral vessels is that traumas from external sources do not permanently deform the stent. Instead, the stent may temporarily deform during an unusually harsh trauma but will spring back to its expanded state once the trauma is relieved. Self-expanding stents, however, are often considered to be less preferred for coronary vessels as compared to balloon-expandable stents. One reason for this is that balloon-expandable stents can be precisely sized to a particular vessel diameter and shape since the ductile metal that is used can be plastically deformed to a desired size and shape. In contrast, self-expanding stents are designed with a particular expansible range. Thus, after being implanted, self-expanding stents continue to exert pressure against the vessel wall.

Self-expanding stents of one class are typically cut from a thin walled nitinol tube. Such a stent is shown, for instance in co-owned U.S. Patent publication 2013/0073052. After being cut, the stent is expanded and heat set to a diameter several times larger than the original tube diameter. With the stent now biased toward the larger diameter, the stent is compressed and loaded into a catheter of a stent delivery system. During the loading procedure, the stent is simultaneously circumferentially compressed and longitudinally compressed in order to push the stent into the catheter of the stent delivery system. Because these stents are cut from relatively thin walled nitinol tubes, there is a risk of substantial deformation and maybe even collapse during the loading procedure. As the industry seeks to manufacture ever smaller diameter stents from thinner walled tubes, problems associated with effective loading of the stent into a delivery system can become acute.

The present disclosure in certain aspects is directed toward one or more of the problems set forth above.

SUMMARY

A stent includes a framework having a length along a stent axis, and includes a sequence of cells that each occupy a discreet segment of the stent length. Each of the cells includes a plurality of struts with ends connected at respective vertices. An adjacent pair of the cells are attached to one another by a plurality of T-bars (or tie bars) that each include a column that defines a long axis extending parallel to the stent axis and a top bar attached to one end of the column. An opposite end of the column is attached to a first cell of the adjacent pair of cells, and the top bar is attached at opposite ends to a second cell of the adjacent pair of cells. In some aspects herein, the hollow cylindrical shape is movable among a loading diameter that is smaller than a tube diameter which is smaller than an expanded diameter, and every strut of the framework is oriented parallel to the stent axis when the hollow cylindrical shape is at the tube diameter. In other aspects herein, the column has a minimum width perpendicular to the long axis that is wider than a maximum width of each of the struts, the column defines at least one slot, and the top bar optionally has a curved edge on a side opposite from the column and the curved edge straddles the long axis. In yet other aspects, the first and second cells of the adjacent pair of cells have defined spacing from one another. Still further aspects that characterize the framework are also disclosed hereinbelow and provide additional embodiments disclosed herein.

In another aspect, a stent includes a framework having a hollow cylindrical shape with a length along a stent axis, and includes a sequence of cells that each occupy a discreet segment of the stent length. Each of the cells includes a plurality of struts with ends connected at respective vertices. The hollow cylindrical shape is moveable among a loading diameter that is smaller than a tube diameter which is smaller than an expanded diameter. Every strut of the framework is oriented parallel to the stent axis when the hollow cylindrical shape is at the tube diameter. Each cell of an adjacent pair of cells of the sequence of cells are on opposite sides of a plane oriented perpendicular to the stent axis when the hollow cylindrical shape is at the tube diameter. The sequence of cells includes at least one end cell, at least one flex cell, and at least one hoop cell.

BRIEF DESCRIPTION OF THE DRAWINGS

FIG. 1 is a flat plan view of a stent at a tube diameter according to the present disclosure;

FIG. 2 is a partial flat plan view of an alternative end structure for a stent according to the present disclosure;

FIG. 7 is a flat plan view of a stent at a tube diameter according to still another embodiment of the present disclosure;

FIG. 8 is an end view of the stent of FIG. 1 showing its hollow cylindrical shape in its expanded diameter;

FIG. 9 is an end view of the stent of FIG. 1 being circumferentially compressed prior to being loaded into a catheter;

FIG. 10 is a side view of the circumferentially compressed stent preparing to be loaded into a catheter;

FIG. 11 is a side view of the stent in a loading configuration partially loaded in the catheter; and FIG. 12 shows the stent after being loaded into the catheter.

DETAILED DESCRIPTION

Figure 3:
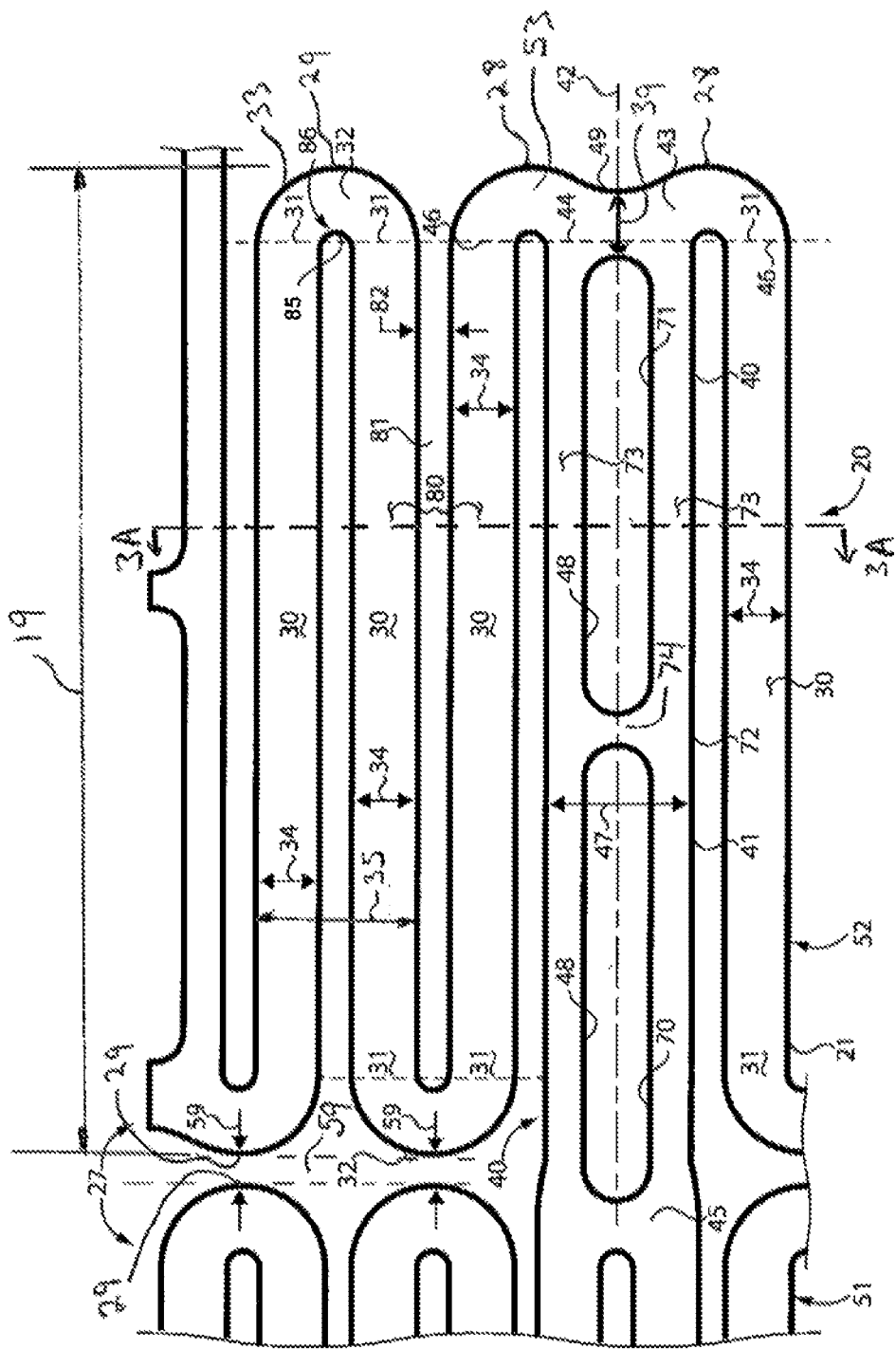
FIG. 3 is an enlarged view of the area 3 shown in FIG. 1.

Although teachings of this disclosure could apply to a wide variety of different sized self expanding stents, the illustrated stents may be for use in a 5 Fr. stent delivery system, and thus are sized to be loaded into a 5 Fr. catheter. The three different illustrated stents include a first stent with an expanded diameter of 4 mm shown in FIGS. 1 and 2, a second stent with an expanded diameter of 5 mm shown in FIGS. 5 and 6, and a third stent with an intended expanded diameter of 6 mm shown in FIG. 7. Because these stents include many features in common, like numbers are used throughout the figures and the following description to identify corresponding features in each of the differently disclosed 5 Fr. stents. As used in the present disclosure, the term "about equal" means that when a ratio of the two quantities is rounded to an integer, that integer is one. Also, it will be well understood that quantities that are disclosed herein as being "about equal to" a specified quantity can also be exactly the specified quantity.

Referring initially to FIGS. 1, 3, 5 and 7, a stent 20 includes a framework 21 having a hollow cylindrical shape shown in a flat plan view with a length 23 along a stent axis 24. Stent 20 is beneficially a self-expanding stent. The framework 21 includes a sequence of cells 25 that each occupy a discrete segment 26 of the stent length 23. Each of the cells 25 includes a plurality of struts 30 with ends 31 connected at respective vertices 32. Each of the cells 25 has a cell length 19. Width 82 is the length of the gap between adjacent struts 30 in the same cell 25. Width 82 between an adjacent pair of struts 30 in a cell can be about equal to a cutting width of the laser used to cut stent 20 from the nitinol or other metallic tube. In the embodiments shown in FIGS. 1, 3, 5 and 7, width 82 can be about equal to 0.05 millimeters. Vertices 32 can be arch shaped members extending between adjacent struts in the same cell 25. Outer edge 33 of vertices 32 can have a diameter equal to width 35 which is equivalent to twice width 34 plus width 82.

Figures 5, 6:
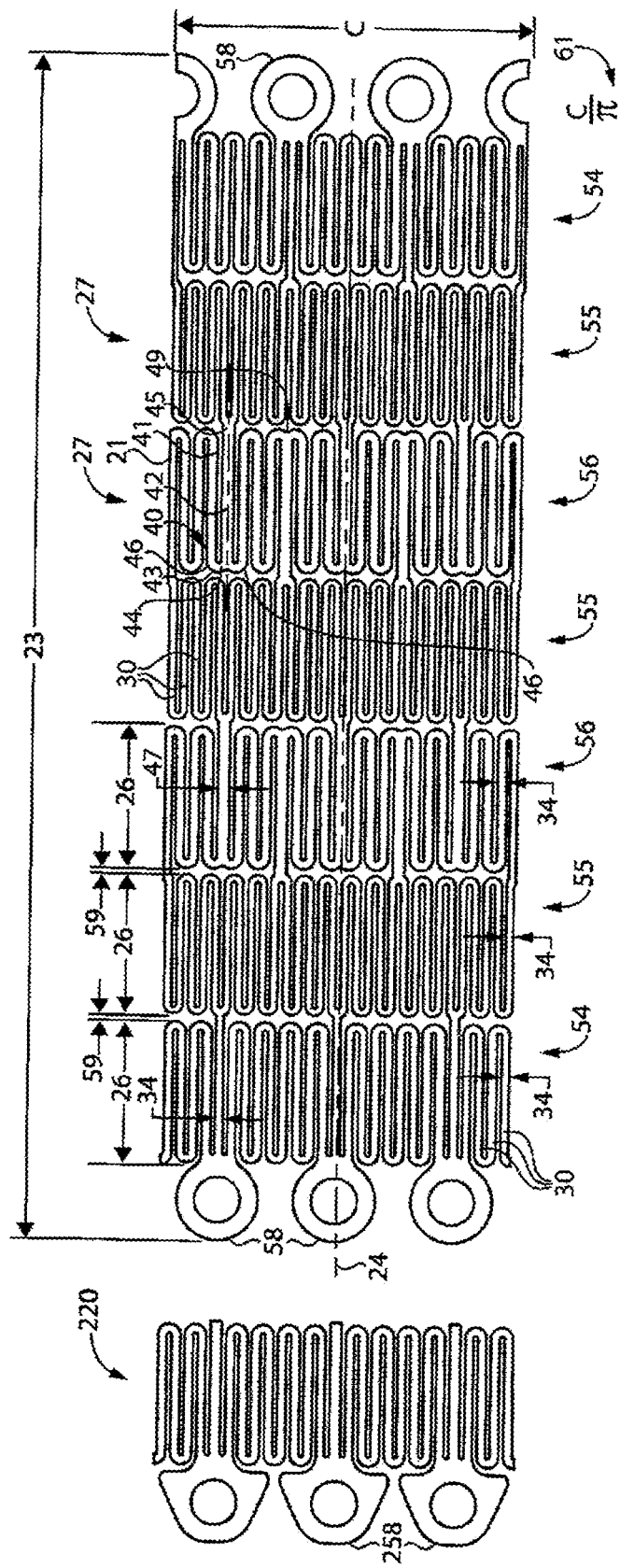
FIG. 5 is a flat plan view of a stent at a tube diameter according to another embodiment of the present disclosure.
FIG. 6 is a partial flat plan view of an alternative end structure for a stent according to the embodiment of FIG. 5.

Preferably, stents 20 are manufactured from a thin walled metallic tube with material laser cut away to render the pattern shown in FIGS. 1, 5 and 7, respectively. For instance, the example stents 20 illustrated in FIGS. 1 and 5 might begin as a nitinol tube with an outer tube diameter of 1.35 millimeters and a wall thickness of 0.12 millimeters. The stent 20 of FIG. 7 might begin as a nitinol tube with an outer tube diameter of 1.35 millimeters and a wall thickness of 0.15 millimeters.

Individual cells 25 may exhibit a relatively high cell surface density in the tube diameter. As used in the present disclosure, the term "cell surface density" means a percentage calculated by dividing the total abluminal or external surface area of the framework 21 elements of a particular cell 25 at the tube diameter by the outer surface area of a solid cylinder having the same outer diameter and length as the particular cell 25, and multiplying by one hundred. In the case of flex cells 55, the cell surface density may be within the range of 60% to 80%, or in the range of 65% to 80%, or in the range of 69% to 71%. In the case of hoop cells 56, the cell surface density may be within the range of 50% to 80%, or in the range of 57% to 78%, or in the range of 62% to 75%. Embodiments herein contemplate stents 20 with frameworks 21 including at least one flex cell 55 having the above-specified cell surface density or multiple flex cells 55 having the above-specified cell surface density, for example two to seventy five such flex cells 55 and potentially all of the flex cells 55 of the framework 21. In addition or alternatively, embodiments herein contemplate stents 20 with frameworks 21 including at least one hoop cell 56 having the specified cell surface density or multiple hoop cells 56 having the specified cell surface density, for example two to seventy five such hoop cells 56 and potentially all of the hoop cells 56 of the framework 21.

Struts 30 are longer than they are wide. Struts 30 can have a length 19 to width 82 ratio in the range of 14 to 20, and in some embodiments have a length 19 to width 82 ratio in the range of 15 to 16, in the range of 16 to 17, in the range of 17 to 18, or in the range of 18 to 19. In addition or alternatively, the cell length 19 for the flex cell(s) 55, hoop cell(s) 56 and end cells 54 of the framework 21 can be in the range of 1.2 to 2 millimeters, or in the range of 1.4 to 1.9 millimeters. It will be understood in these regards that the length 19 to width 82 ratios for the struts 30 and/or cell lengths 19 can be the same for the end cells 54, flex cells 55 or hoop cells 56 of the framework 21 or can vary among the cells 54, 55 or 56 of the framework 21. In some forms, the length to width ratios for the struts 30 and/or the cell lengths 19 will be the same for the end cells 54 of the framework 21, and/or will be the same for all flex cells 55 of the framework 21, and/or will be the same for all hoop cells 56 of the framework 21.

The illustrated embodiments show stents 20 with a sequence of seven cells 25, with each adjacent pair of cells 27 being separated by a cell separation distance 59 (at the tube diameter as illustrated), which may be about equal to a cutting width of the laser used to cut stent 20 from the nitinol tube. In addition or alternatively, cell separation distance 59 at the tube diameter can be less than 0.08 millimeters, for example in the range of 0.04 to 0.08 millimeters, or in the range of 0.04 to 0.06 millimeters, and in some forms approximately 0.05 millimeters. In a specific example of FIGS. 1, 5 and 7, the laser cutting width and the cell separation distance 59 may be 0.05 millimeters. Note that stents 20 can optionally include additional cells. For example, in one embodiment, stent 20 may include between twenty three and twenty eight cells 25. In another embodiment, stent 20 may include between forty eight and fifty four cells 25. In yet another embodiment, stent 20 may include between seventy four and eighty cells 25. Any number of cells 25 can be utilized to achieve desired performance parameters and length 23. In general, stent 20 can include between ten and one hundred fifty cells, between thirty and one hundred thirty cells and between forty and one hundred twenty cells. As an example, stent 20 can include between one and seventy five hoop cells 56 and/or between one and seventy five flex cells 55. As an example, length 23 can be between ten and two hundred millimeters or between thirty and one hundred fifty millimeters.

An adjacent pair of the cells 27 may be attached to one another by a plurality of T-bars 40 (or tie bars) that each include a column 41 attached at one end 44 to a top bar 43. Top bar 43 couples column 41 to adjacent struts 30 positioned on either side of the column 41. The column 41 defines a long axis 42 that extends parallel to the stent axis 24. An opposite end 45 of the column 41 is attached to a first cell 51 of the adjacent pair cells 27, and the top bar 43 is attached at opposite ends 46 to a second cell 52 of the adjacent pair of cells 27. The column 41 has a minimum width 47 perpendicular to the long axis 42 that is wider than a maximum width 34 of each of the struts 30. In the case of the FIG. 1 embodiment, the column 41 defines at least one slot 48. Minimum width 47 can be less than width 35 of an adjacent pair of struts 80. Minimum width 47 can also be greater than or equal to width 34 of struts 30. In the FIG. 1 embodiment, each column 41 defines exactly two slots 70 and 71 that each are equally sized, are separated by bridge 74, share a common centerline and have long dimensions extending along long axis 42. Other embodiments contemplate a single slot defined in some or all columns 41 of the framework 21, or multiple slots (for example two to five slots) defined in some or all columns 41 of the framework 21, including embodiments in which the number of slots in different columns 41 of the framework is the same or varies.

As illustrated in FIGS. 1 and 3, at least in the tube diameter 61, the slots 70 of columns 41 extend into (and completely through) the gaps between adjacent cells 25 defined by cell separation distances 59. Embodiments herein contemplate stent frameworks 21 in which the T-bars 40 connecting at least one adjacent pair of cells 25 of the framework 21 that does not include an end cell 54, have columns 41 that each have one or more slots defined therein (for example a single slot, one to five slots longitudinally spaced from one another, or exactly two slots longitudinally spaced from one another), wherein at least one of the one or more slots defined by each such column 41 extends into and optionally completely through the gaps between adjacent cells defined by cell separation distances 59. In further embodiments, these specified slotted T-bar geometries can be present in the T-bars 40 connecting a majority of, or all of, the cells 25 of the framework that are not end cells 54.

In all the three illustrated embodiments of FIGS. 1, 5 and 7, the top bar 43 has a curved edge 49 located on an opposite side from column 41. The curved edge 49 may be a concave edge that faces away from the column 41 and straddles the long axis 42. The curvature of curved edge 49 means that the edge surface bound by the inner and outer tube surfaces has portions on both sides of a plane perpendicular to stent axis 24. In general, ends 45 of T-bars 40 are attached to a longitudinal extension from an adjacent pair of struts 80 that are positioned in a cell 25 adjacent to the cell 25 in which the T-bar 40 is positioned. Conversely, end 44 is generally coupled to a pair of struts 30 that are positioned in the same cell 25 through which T-bar 40 extends, with a strut 30 positioned on either side of the T-bar 40 with a lateral connection 53 such as top bar 43 or eyelet 58 connecting both struts 30 and the T-bar 40 together at the lateral connection 53. T-bars 40 are generally parallel to struts 30 in the same cell. While the embodiments disclosed herein show top bar 43 as being a unitary structure between both struts 30, it does not have to be unitary. Optionally top bar 43 could be bifurcated, with one portion attaching T-bar 40 to one strut 30 and another portion attaching T-bar 40 to the other strut 30.

Figure 4:
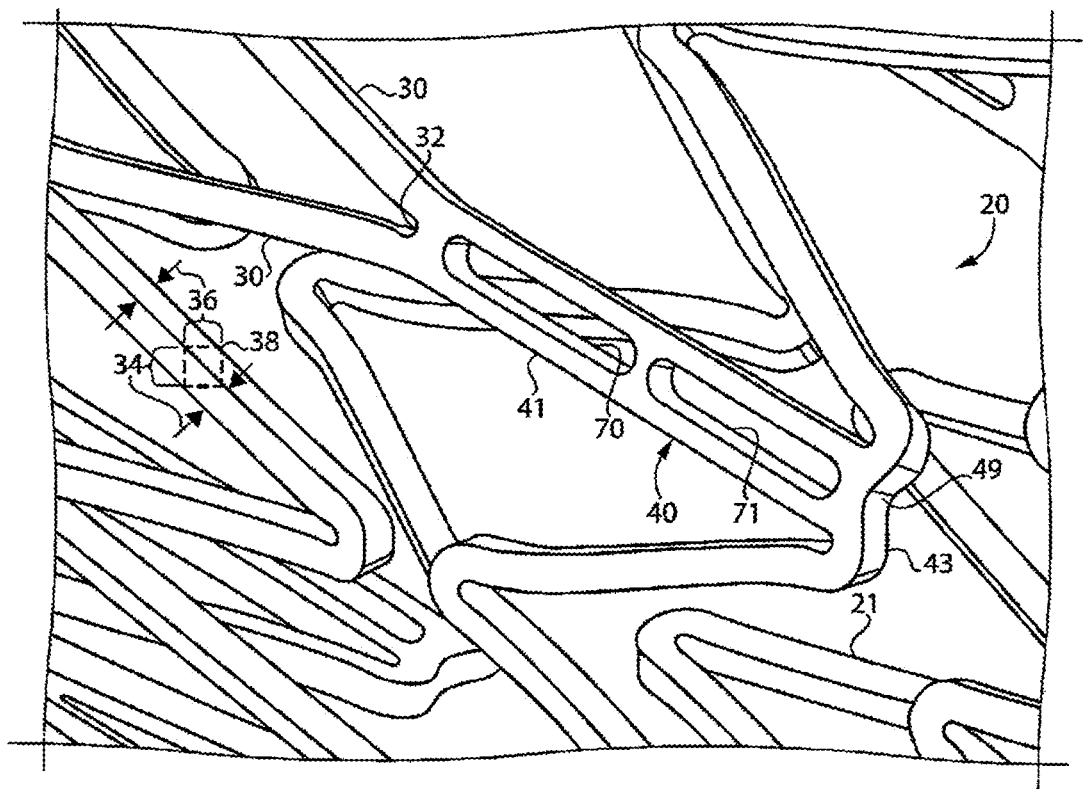
FIG. 4 is a partial view of the stent of FIG. 1 shown in an expanded diameter.
Figure 13:
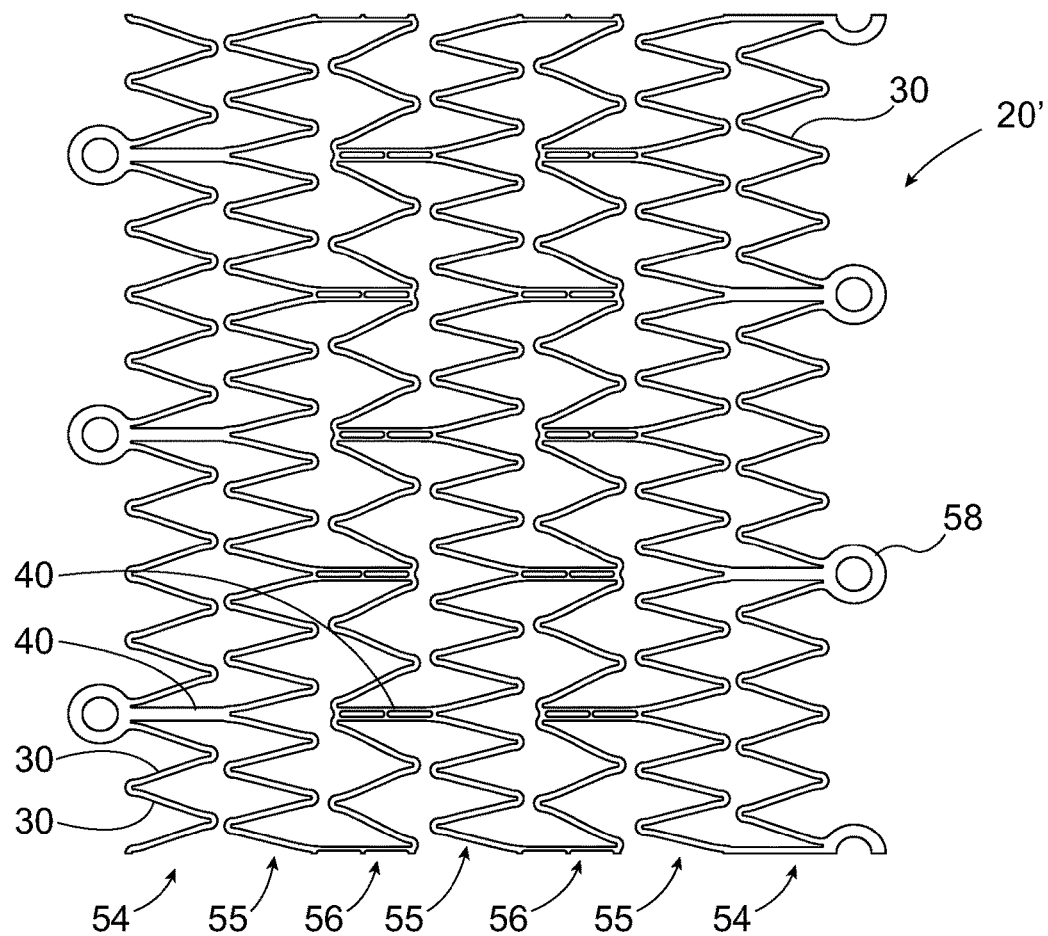
FIG. 13 is a flat plan view of the FIG. 1 stent expanded to a 4 mm expanded diameter.
Figure 14:
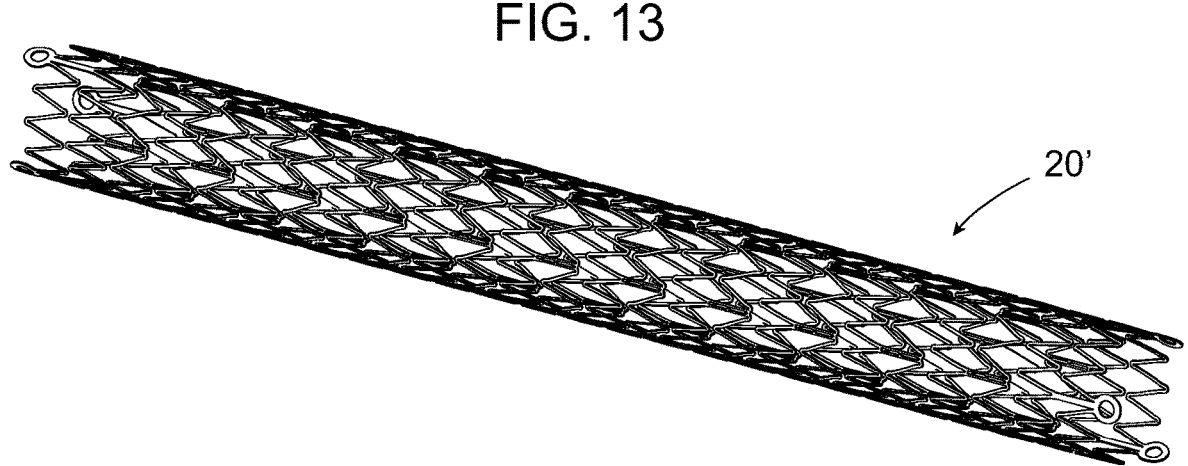
FIG. 14 is a perspective view of the FIG. 1 stent expanded to a 4 mm expanded diameter.

Referring in addition to FIGS. 4 and 8, after the metallic tube is cut into a stent 20 as shown in FIG. 1, the hollow cylindrical shape 22 is expanded to an expanded diameter 62, which in this case may be 4 millimeters, and then heat set at that expanded diameter 62. A view of the FIG. 1 stent 20 at expanded diameter 62 is illustrated in FIG. 13 as expanded stent 20' shown in a flat plan view. FIG. 14 illustrates a hollow cylindrical view of stent 20' at expanded diameter 62. The embodiments of FIGS. 5 and 7 may be heat set at expanded diameters 62 of 5 and 6 millimeters respectively. The result being that the framework 21 is now biased toward the expanded diameter 62. Thus, during one typical manufacture, the stent 20 starts out at a tube diameter 61 (circumference C/π) that is smaller than an expanded diameter 62 at which the stent is heat set. Later, the stent 20 is then compressed to a loading diameter 60, which is smaller than the tube diameter 61 in certain embodiments, for loading into a stent delivery system. Although the advanced T-bar structure and geometry of the present disclosure could scale to virtually any sized stent, the present disclosure and the illustrated embodiments are taught in the context of a stent 20 having a tube diameter 61 of 5 Fr. or less.

In order to provide more longitudinal support when the stent 20 is loaded into a stent delivery system, every strut 30 of the framework 21 is oriented parallel to the stent axis 24 when the hollow cylindrical shape 22 is at the tube diameter 61, as shown in FIGS. 1, 5 and 7. As per the illustrated embodiments, each of the struts 30 may have a uniform width 34, a uniform thickness 36 (i.e., the wall thickness of the pre-cut tube as potentially modified by stent manufacturing steps such as polishing) and a rectangular cross section 38. Or, struts may have such uniform geometry in a given cell (see FIGS. 5 and 7), but struts in different cells may be wider than struts in a different cell of the same stent as in FIGS. 5 and 7. The ratio of the strut width 34 to the strut thickness 36 may be about equal to one. In addition or alternatively, the thicknesses 36 of the struts 30 of the framework can be within the range of 85 to 135 microns, or in the range of 90 to 125 microns, or in the range of 95 to 105 microns. Similar thickness ranges can apply to the other components of the framework 21, including the T-bars 40, vertices 32 and eyelets 58. Each adjacent pair of struts 80 may be separated by a rectangular space 81 with a width 82 that is less than a width 34 of each of the adjacent pair of struts 30 when the hollow cylindrical shape 22 is at the tube diameter 61. Although not necessary, the width 82 of the rectangular space 81 may be equal to the width of the laser used to cut stent 20 from the metallic tube, as discussed earlier.

Each of the vertices 32 that connect adjacent struts 30, may define a continuous inner curve 85 with a radius 86 that may be less than one half of a width 34 of the struts 30 joined by the respective vertex 32. Each vertex 32 defines a peak 29. The cell separation distance 59 occurs between opposed peaks 29 on adjacent cells 25, and defines a gap between adjacent cells 25. In the case of the FIG. 1 embodiment, the column 41 of the T-bars 40 may have a tall H shape 72, with each leg 73 of the H shape 72 being less than a width 34 of each of the struts 30. In all the illustrated embodiments, the top bar 43 is shown as having a concave edge 49 that faces away from the column 41 and straddles long axis 42. Top bar 43 defines width 39 at the narrowest point between slot 71 and concave edge 49. In one embodiment, width 39 can be equal to width 34. In another embodiment, width 39 can be less than width 34. Top bar 43, with concave edge 49, also defines two peaks 28, one on either side of concave edge 49. The present disclosure contemplates any curved edge, including convex, on a side of the T-bar that is opposite from the column 41. In one embodiment, concave edge 49 could extend further into slot 71, more completely bifurcating top bar 43 into two peaks (e.g. with outer contours resembling the contours formed by outer edges 33).

An individual peak 29 or 28 of a first cell 25 can be longitudinally aligned with an oppositely facing individual peak 29 or 28 of a second cell 25 adjacent to the first cell (across the gap defined by the cell separation distance 59). In one example, a first cell 25 and a second cell 25 have the same total number of peaks (the sum of any and all peaks 28 and 29) as one another, and each of the peaks of the first cell 25 is longitudinally aligned with a corresponding oppositely facing peak of the second cell, such as the configuration shown in FIG. 1. However, other embodiments include some offset from longitudinal alignment of oppositely facing peaks 28 and 29 between first and second adjacent cells 25, such as the configurations shown in FIGS. 5 and 7. Such offsets from longitudinal alignment can in some forms be limited to a distance that is less than 20 percent of width 35 (the width of an adjacent pair of struts 80), or in some forms less than 10 percent of width 35. In some embodiments, at least first and second cells 25 of an adjacent pair of cells in the overall stent framework 21 defining the length of stent 20 can have the above-described longitudinal alignment and/or longitudinal alignment offset features, for example at least one flex cell 55 adjacent to a hoop cell 56. In other embodiments, at least four consecutive cells 25 of the overall stent framework 21 defining the length of stent 20 can have the above-described longitudinal alignment and/or longitudinal alignment offset features. In still other embodiments, the majority of, or all of, the cells 25 of the overall stent framework 21 defining the length 23 of the stent 20 can have the above-described longitudinal alignment and/or longitudinal alignment offset features.

Although a stent 20 according to the present disclosure can include any number of cells 25, the illustrated embodiments show stents 20 with a sequence of seven cells 25 that include an end cell 54 on each end, a flex cell 55 immediately adjacent each of the end cells 54 and two hoop cells 56, with a single flex cell 55 positioned between the two hoop cells 56. Although the end cells 54 could conceivably utilize the T-bar structure taught in this disclosure for connection to an adjacent cell 25, the adjacent pair of cells 27 that are connected by T-bars 40 according to the illustrated embodiment includes exactly one flex cell 55 and exactly one hoop cell 56. Each cell 25 of an adjacent pair of cells 27 is on opposite sides of a plane oriented perpendicular (in and out of page) to the stent axis 24.

The structure of the end cells 54, Flex cells 55 and hoop cells are different from one another. Hoop cells 56 can provide higher radial force but be less flexible than either flex cells 55 or end cells 54. Flex cells 55 can provide less radial force but be more flexible than either hoop cells 56 or end cells 54.

Flex cells 55 can have smaller strut widths 34 than hoop cells 56 and/or can have more struts 30 than hoop cells 56. Conversely, hoop cells 56 can have greater strut widths 34 and/or can have fewer struts 30 than flex cells 55. In some embodiments, at least 3 T-bars (e.g. from three to six T-bars), or exactly three T-bars, connect each adjacent cell 25 together, and are preferably evenly spaced around the circumference of the framework 21.

Although not necessary, the frame work 21 can terminate in a plurality of eyelets 58. These eyelets could be omitted without departing from the scope of the present disclosure. Preferably, and especially in the context of smaller diameter stents such as 5 French or less, the framework 21 may terminate in exactly three eyelets 58. FIG. 2 shows an alternative stent structure 120 with rectangular shaped eyelets 158 that also fall within the intended scope of this disclosure. FIG. 6 also shows an alternative stent structure 220 with different shaped eyelets 258 that also fall within the scope of this disclosure.

The T-bar 40 structure and/or other geometry of the present disclosure is believed, along with the other features of stent 20, to maintain good stent performance requirements without undermining the ability of the stent to be loaded into a delivery system. Loading involves compressing the stent 20 down below its tube diameter to a loading diameter, and then pushing the stent out of a compression head and into a delivery system. The reason that loading can be challenging is because the stents are designed to have high radial stiffness in order to help maintain vessel patency after deployment, while maintaining substantial flexibility in other modes of deformation (axial, bending and torsion) in order to achieve good fatigue performance in the body. The present disclosure recognizes that one area of stent geometry that can strongly influence packing density and hence loadability without negative consequences to other stent performance aspects are the geometry and structure of the T-bars 40. The present disclosure recognizes that the width 47 of the column 41 and width of the top bar 43 can be made wider without compromising stent performance in other areas. The T-bars 40 of the present disclosure can also utilize material removal via at least one slot (FIG. 1) along their long axis 42 centerlines to improve circumferential bending performance that benefits certain stages of stent manufacturing. Specifically, during the manufacture of stents 20, fractures and cracks can occur in the region where the struts 30 merge with the top bar 43 of the T-bars 40. This stress can be caused by the high circumferential stiffness of a wide T-bar. By removing material from the central region of the top bar 43, which is shown in the illustrated embodiment by the concave edge 49, adequate circumferential stiffness is alleviated to allow small diameter thin walled stents to be manufactured and undergo expansion and heat-setting operations without cracking. Thus, an alternative to the concave edge 49 shown could be to have that surface of the top bar 43 be made convex instead. For instance, with regard to the embodiment of FIG. 1, material removal according to the teaching of the present disclosure to address circumferential stiffness could be achieved by possibly extending the length of slot 71 along long axis 42 to reduce the amount of material that makes up top bar 43. Alternatively, material could be removed from the thickness of column 41 and/or top bar 43 using a material removal technique such as ablation with a laser to optionally reduce the wall thickness while not creating an opening through column 41 and/or top bar 43 while adjusting the stiffness of column 41 and/or top bar 43.

Many of the characteristics of stent 20 disclosed herein seek to facilitate relatively uniform strain in individual portions of stent 20, particularly when repeatedly expanding stent 20 and, after being set at the expanded diameter, when later compressed for loading into a catheter. Examples include using curved surfaces at all transitions, use of similar cross-sectional areas (thickness×width) where bending occurs and removal of material where necessary.

Figure 3A:
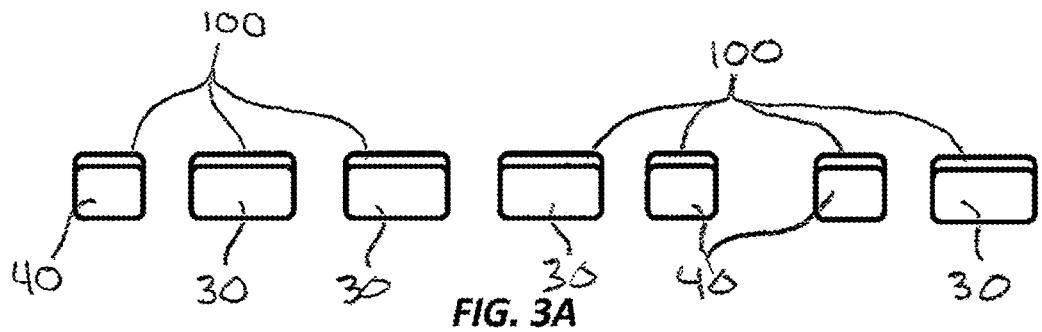
FIG. 3A is a cross sectional view of a first alternative embodiment of the stent with an added abluminal surface coating layer, shown as taken along line 3A-3A in FIG. 3.
Figure 3B:
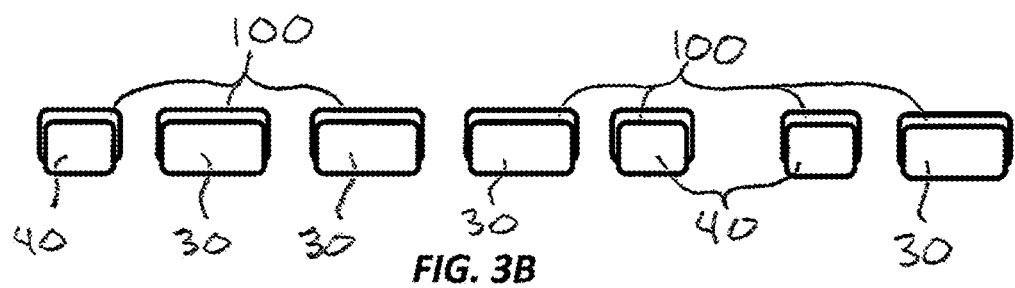
FIG. 3B is a cross sectional view of a second alternative embodiment of the stent with an added abluminal and side surface coating layer, shown as taken along line 3A-3A in FIG. 3.
Figure 3C:
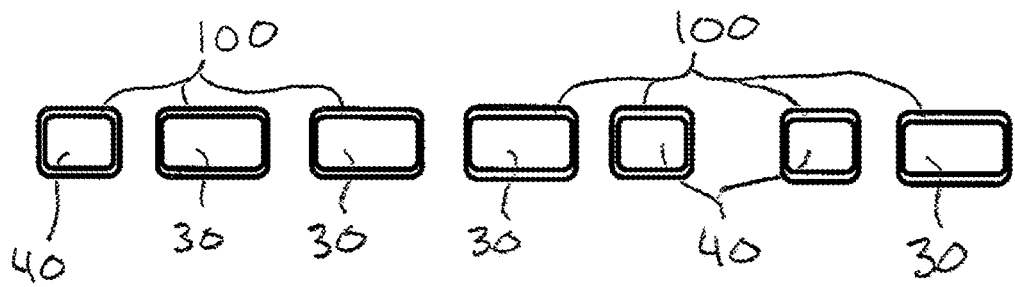
FIG. 3C is a cross sectional view of a third alternative embodiment the stent with an added circumferential surface coating layer, shown as taken along line 3A-3A in FIG. 3.

In other embodiments herein, at least a portion of the surface of the framework 21 can have a coating layer 100 thereover (see e.g. FIGS. 3A, 3B and 3C). For example, part or all of the surfaces of the struts 30 and/or vertices 32 and/or the T-bars 40 of the framework can be covered with a coating layer 100. In some forms, the coating layer 100 can include a therapeutic agent, such as a restenosis-inhibiting agent. The restenosis-inhibiting agent may, for example, be: a microtubule stabilizing agent such as paclitaxel, a paclitaxel analog, or a paclitaxel derivative or other taxane compound; a macrolide immunosuppressive agent such as sirolimus (rapamycin), pimecrolimus, tacrolimus, everolimus, zotarolimus, novolimus, myolimus, temsirolimus, deforolimus, or biolimus. In addition or alternatively, the coating layer 100 can include a polymer matrix, for example a polymer matrix comprising or constituted of a biodegradable polymeric material. Such a biodegradable polymeric material may include a single biodegradable polymer or a mixture of biodegradable polymers. Examples of biodegradable polymers include polycaprolactone, polylactic acid homopolymers, polylyactic acid copolymers such as a polyglycolic acid/polylactic acid copolymer, polyhydroxybutarate valerate, polyorthoester and polyenthylenoxide/polybutylene terephthalate. Those of skill in the art will understand that other biodegradable polymers or non-biodegradable polymers are also available and can be used.

The therapeutic agent can be incorporated in the coating at any suitable level. Typically, when the therapeutic agent is a restenosis-inhibiting agent such as any of those disclosed above, it will be incorporated in the coating at a level of about 0.01 to about 50 micrograms per $mm^2$, and in certain forms about 0.5 to about 10 micrograms per $mm^2$. The thickness of the coating layer 100 is typically from about 1 micron to about 30 microns, or from about 1 to about 10 microns.

With reference now specifically to FIGS. 3A, 3B and 3C, the coating layer 100 in some embodiments can cover at least the abluminal surfaces, or only the abluminal surfaces (see FIG. 3A), or only the abluminal and all or a portion of the side surfaces (see FIG. 3B), or the complete circumferential surfaces (see FIG. 3C), of the struts 30 and T-bars 40 of the framework 21. In corresponding fashion, the coating layer 100 can in addition cover at least the abluminal surfaces, or only the abluminal surfaces, or only the abluminal and all or a portion of the side surfaces, or the complete circumferential surfaces, of the vertices 32, eyelets 58, 158 or 258, and/or other structures of the framework 21. In some forms, all or essentially all (90% or more of) the abluminal, side and luminal surfaces of the framework 21 are covered by the coating layer 100.

In beneficial coated stent embodiments herein, the struts 30 have a thickness 36 in the range of 85 to 135 microns, and the combined thickness of the coating layer 100 and the strut 30 can be greater than the strut thickness 36 but not exceed 150 microns, and such combined thickness can in some forms be in the range of 95 to 140 microns. Similar values can be present for the combined thickness of the coating layer 100 and the T-bars 40 and/or for the combined thickness of the coating layer 100 and the vertices 32. It will be understood that these values for combined thickness can be present in each of the embodiments disclosed in connection with FIGS. 3A, 3B and 3C, with the combined thickness in the case of the circumferential coating shown in FIG. 3C including the sum of the thickness of the coating 100 on the abluminal surface, the thickness of the coating 100 on the luminal surface (opposite the abluminal surface), and the strut thickness 36, with similar values being applicable in respect of coated T-bars 40 and/or coated vertices 32 and/or coated other structures of the framework 21 when present.

In additional embodiments, the struts 30 will have a thickness 36 in the range of 90 to 125 microns, and the ratio of the combined thickness of the coating 100 and the struts 30 to the thickness 36 of the struts 30 alone will be in the range of 1.2:1 to 1.05:1, or in the range of 1.15:1 to 1.05:1. Again, in embodiments where the T-bars 40 and/or vertices 32 and/or other framework 21 structures are also coated, similar ratio values can apply to their respective thicknesses and the coating layer 100. As before, it will be understood that these ratio values can be present in each of the embodiments disclosed in connection with FIGS. 3A, 3B and 3C, with the combined thickness in the case of the circumferential coating shown in FIG. 3C including the sum of the thickness of the coating 100 on the abluminal surface of the struts 30, the thickness of the coating 100 on the luminal surface of the struts 30, and the thickness of the struts 30 themselves (with similar ratio values being applicable in respect of coated T-bars 40 and/or coated vertices 32 and/or coated other framework 21 structures when present).

Referring now in addition to FIGS. 9-12, a loading procedure for a stent 20 according to the present disclosure is schematically illustrated. The loading procedure begins by circumferentially compressing the stent down to a loading diameter 60 that is smaller than the tube diameter 61. For instance, in one specific example, the tube diameter could be 1.35 millimeters for a 5 French stent, and the corresponding loading diameter might be 1.34 millimeters (see FIG. 9). The circumferentially compressed stent is then moved toward loading into a catheter 11 of a stent delivery system 10 as shown in FIG. 10 with a device identified as a compression head. Next, a force F is applied to push the stent 20 into catheter 11 while maintaining the circumferential compression. The result of this is to put stent 20 into a loading configuration 15 in which the stent is simultaneously compressed circumferentially and longitudinally while the stent 20 is slid into the catheter 11. This longitudinal stress may cause adjacent cells 25 to move from out of contact into contact responsive to the longitudinal compression. This contact between adjacent cells 25 is believed to provide additional column strength and longitudinal rigidity to the stent 20 while being loaded to avoid undesirable outcomes, such as buckling or other undesirable deformations during the loading process. The longitudinal compression on stent 20 during the loading procedure may be a consequence of stent friction interaction with the interior wall of catheter 11 while the pushing force F is applied to facilitate loading. After the loading procedure is complete, one could expect the longitudinal geometry of the stent to resiliently resume the separation distance 59 between adjacent cells 25 after the longitudinal compression is relieved.

By utilizing wide top bars 43, the individual struts 30 can be oriented parallel to the stent axis when the hollow cylindrical shape 22 is at the tube diameter 61. This helps to permit each of the struts 30 to carry a fraction of the longitudinal loading compression in parallel with the longitudinal loading push force F. The columns 41 of the T-bars 40 can be made less stiff in the circumferential direction by material removal through the inclusion of slots 70 and 71 (FIG. 1) and/or by the curved shape of the T-bars 40. Thus, the slots 70 and 71 can locally reduce stiffness, allow more uniform bending, and prevent or inhibit the appearance of cracks during heat setting at an expanded diameter 62.

INDUSTRIAL APPLICABILITY

The present disclosure finds general applicability in self expanding stents. More particularly, the teachings of the present disclosure are specifically applicable to smaller diameter self expanding stents, such as those having diameters of five French or less. These smaller diameter stents might find application in, for instance, arteries in the lower leg of a patient. Although the stent 20 in the present disclosure has been illustrated in the context of being manufactured from a thin walled tube of nitinol, such as superelastic nitinol, the present disclosure also contemplates stents made from other appropriate materials, such as other superelastic metals or biodegradable polymers that exhibit superelastic traits similar to nitinol.

The 5 mm (FIG. 5) and 6 mm (FIG. 7) stent designs are similar to each other and to the 4 mm (FIG. 1), but each have unique cell lengths and may have differing wall thicknesses. Cell length finds an analogy to strut length. Unique cell lengths and wall thickness values may be necessary to achieve the appropriate radial force and axial/bending/torsional flexibility for good fatigue performance for each stent diameter. Utilization of parallel laser cuts and associated parallel struts, along with a thin cutting space between cells can be expected to benefit the loading for other stent sizes as well, especially if the stents are designed to achieve a high radial force. This may be because stents with high radial force, but highly flexible in other modes (axial, bending and torsion to promote good fatigue in those modes) generally may have low column strength, meaning that these high radial force thin-walled stents are compressed and pushed into the delivery system they may buckle under the axial pushing force. Tight spacing of the struts and cells enhances column strength, reducing the potential for buckling during loading. Parallel cuts and the associated parallel struts along with low spacing between cells may be a particular benefit to even lower French sized stents including 4 Fr., 3 Fr., and may be even associated small stent diameters as low as 1 mm.

The present is for illustrative purposes only, and should not be construed to narrow the breadth of the present disclosure in any way. Thus, those skilled in the art will appreciate that various modification might be made to the presently disclosed embodiments without departing from the full and fair scope and spirit of the present disclosure. Other aspects, features and advantages will be apparent upon an examination of the attached drawings and appended clauses and claims.

Clause 1. A stent comprising: a framework having a hollow cylindrical shape with a length along a stent axis, and the framework including a sequence of cells that each occupy a discrete segment of the stent length, and each of the cells including a plurality of struts with ends connected at respective vertices; an adjacent pair of the cells being attached to one another by a plurality of T-bars that each include a column defining a long axis extending parallel to the stent axis and a top bar attached to one end of the column, and an opposite end of the column being attached to a first cell of the adjacent pair of cells, and the top bar being attached at opposite ends to a second cell of the adjacent pair of cells; wherein the hollow cylindrical shape is movable among a loading diameter that is smaller than a tube diameter which is smaller than an expanded diameter; every strut of the framework is oriented parallel to the stent axis when the hollow cylindrical shape is at the tube diameter.

Clause 2. The stent of clause 1 wherein each adjacent pair of struts of the plurality of struts is separated by a distance that is less than a width of each of the pair of struts when the hollow cylindrical shape is at the tube diameter.

Clause 3. The stent of any one of clauses 1-2 wherein the column has a minimum width perpendicular to the long axis that is wider than a maximum width of each of the plurality of struts.

Clause 4. The stent of any one of clauses 1-3 wherein the top bar has a curved edge on a side opposite from the column and the curved edge straddles the long axis.

Clause 5. The stent of any one of clauses 1-4 wherein each of the plurality of struts has a width to thickness ratio about equal to one.

Clause 6. The stent of any one of clauses 1-5 wherein the framework is biased toward the expanded diameter; and the tube diameter is sized to fit within a 5 French catheter.

Clause 7. The stent of any one of clauses 1-6 wherein the sequence of cells includes at least one end cell, at least one flex cell, and at least one hoop cell; and the adjacent pair of cells includes exactly one flex cell and exactly one hoop cell.

Clause 8. The stent of any one of clauses 1-7 wherein each adjacent pair of cells in the sequence of cells is separated by a distance that is less than a minimum width of every strut of the plurality of struts.

Clause 9. The stent of any one of clauses 1-8 wherein each end of the framework terminates in exactly three eyelets.

Clause 10. The stent of any one of clauses 1-9 wherein the framework is biased toward the expanded diameter, which is four millimeters.

Clause 11. The stent of any one of clauses 1-10 wherein the framework is biased toward the expanded diameter, which is five millimeters.

Clause 12. The stent of any one of clauses 1-11 wherein the framework is biased toward the expanded diameter, which is six millimeters.

Clause 13. The stent of any one of clauses 1-12 wherein each cell of an adjacent pair of cells of the sequence of cells are on opposite sides of a plane oriented perpendicular to the stent axis when the hollow cylindrical shape is at the tube diameter.

Clause 14. The stent of any one of clauses 1-13 wherein adjacent cells of the sequence of cells contact each other when the framework is in a loading configuration.

Clause 15. The stent of any one of clauses 1-14 wherein each of the plurality of struts has a uniform width, a uniform thickness, and a rectangular cross section.

Clause 16. The stent of any one of clauses 1-15 wherein each of the vertices define a continuous inner curve with a radius that is less than a width of the struts joined by a respective vertex of the vertices.

Clause 17. The stent of any one of clauses 1-16 wherein the top bar has a curved edge on a side opposite from the column, and the curved edge is a concave edge that faces away from the column.

Clause 18. A stent comprising: a framework having a hollow cylindrical shape with a length along a stent axis, and the framework including a sequence of cells that each occupy a discrete segment of the stent length, and each of the cells including a plurality of struts with ends connected at respective vertices; wherein the hollow cylindrical shape is movable among a loading diameter that is smaller than a tube diameter which is smaller than an expanded diameter; every strut of the framework is oriented parallel to the stent axis when the hollow cylindrical shape is at the tube diameter; each cell of an adjacent pair of cells of the sequence of cells are on opposite sides of a plane oriented perpendicular to the stent axis when the hollow cylindrical shape is at the tube diameter; and the sequence of cells includes at least one end cell, at least one flex cell, and at least one hoop cell.

Clause 19. The stent of clause 18 wherein each adjacent pair of struts of the plurality of struts is separated by a distance that is less than a width of each of the pair of struts when the hollow cylindrical shape is at the tube diameter.

Clause 20. The stent of any one of clauses 18-19 wherein adjacent cells of the sequence of cells contact each other when the framework is in a loading configuration.

Clause 21. The stent of any one of clauses 18-20 wherein each of the plurality of struts has a uniform width, a uniform thickness, and a rectangular cross section.

Clause 22. A stent comprising: a framework having a hollow cylindrical shape with a length along a stent axis, and the framework including a sequence of cells that each occupy a discrete segment of the stent length, and each of the cells including a plurality of struts with ends connected at respective vertices; an adjacent pair of the cells being attached to one another by a plurality of T-bars that each include a column defining a long axis extending parallel to the stent axis and a top bar attached to one end of the column, and an opposite end of the column being attached to a first cell of the adjacent pair of cells, and the top bar being attached at opposite ends to a second cell of the adjacent pair of cells; the column has a minimum width perpendicular to the long axis that is wider than a maximum width of each of the struts, and the column defines at least one slot; and the top bar has a curved edge on a side opposite from the column and the curved edge straddles the long axis.

Clause 23. The stent of clause 22 wherein each of the struts has a width to thickness ratio about equal to one.

Clause 24. The stent of any one of clauses 22-23 wherein the hollow cylindrical shape is movable among a loading diameter that is smaller than a tube diameter which is smaller than an expanded diameter; the framework is biased toward the expanded diameter; and the tube diameter is 5 French or less.

Clause 25. The stent of any one of clauses 22-24 wherein the at least one slot is exactly two slots.

Clause 26. The stent of any one of clauses 22-25 wherein every strut of the framework is oriented parallel to the stent axis when the hollow cylindrical shape is at a tube diameter.

Clause 27. The stent of any one of clauses 22-26 wherein the sequence of cells includes at least one end cell, at least one flex cell, and at least one hoop cell; and the adjacent pair of cells includes exactly one flex cell and exactly one hoop cell.

Clause 28. The stent of any one of clauses 22-27 wherein each end of the framework terminates in exactly three eyelets.

Clause 29. The stent of any one of clauses 22-28 wherein adjacent cells of the sequence of cells contact each other when the framework is in a loading configuration.

Clause 30. The stent of any one of clauses 22-29 wherein the column has a tall H shape, with each leg of the H shape is less than a width of the struts.

Clause 31. The stent of any one of clauses 22-30 wherein each of the struts has a uniform width, a uniform thickness, and a rectangular cross section.

Clause 32. The stent of any one of clauses 22-31 wherein each adjacent pair of struts is separated by a rectangular space with a width that is less than a width of each of the adjacent pair of struts when the hollow cylindrical shape is at a tube diameter.

Clause 33. The stent of any one of clauses 22-32 wherein each of the vertices define a continuous inner curve with a radius that is less than one half of a width of the struts joined by a respective vertex of the vertices.

Clause 34. The stent of any one of clauses 22-33 wherein the curved edge is a concave edge that faces away from the column.

Clause 35. The stent of any one of clauses 22-34 wherein the hollow cylindrical shape is movable among a loading diameter that is smaller than a tube diameter which is smaller than an expanded diameter; the framework is biased toward the expanded diameter; and every strut of the framework is oriented parallel to the stent axis when the hollow cylindrical shape is at a tube diameter.

Clause 36. The stent of any one of clauses 22-35 wherein each of the struts has a width to thickness ratio about equal to one.

Clause 37. The stent of any one of clauses 22-36 wherein the sequence of cells includes at least one end cell, at least one flex cell, and at least one hoop cell; and the adjacent pair of cells includes exactly one flex cell and exactly one hoop cell.

Clause 38. The stent of any one of clauses 22-37 wherein each of the struts has a uniform width, a uniform thickness, and a rectangular cross section.

Clause 39. The stent of any one of clauses 22-38 wherein adjacent cells of the sequence of cells contact each other when the framework is in a loading configuration.

Clause 40. A method of loading a self expanding stent into a catheter of a stent delivery system, comprising the steps of: putting the stent in a loading configuration, which includes simultaneously compressing the self expanding stent circumferentially and longitudinally while sliding the stent into the catheter; and moving adjacent cells of the self expanding stent from out of contact into contact responsive to the longitudinal compression.

Clause 41. The method of clause 40, wherein the circumferential compression includes moving a hollow cylindrical shape of the self expanding stent from a tube diameter to a loading diameter; and every strut of the self expanding stent is parallel to every other strut of the self expanding strut at the tube diameter.

Clause 42. A stent comprising: a framework having a hollow cylindrical shape with a length along a stent axis, and the framework including a sequence of cells that each occupy a discrete segment of the stent length, and each of the cells including a plurality of struts with ends connected at respective vertices; an adjacent pair of the cells being attached to one another by a plurality of T-bars that each include a column defining a long axis extending parallel to the stent axis and a top bar attached to one end of the column, and an opposite end of the column being attached to a first cell of the adjacent pair of cells, and the top bar being attached at opposite ends to a second cell of the adjacent pair of cells.

Clause 43. The stent of clause 42, wherein each of the vertices define a peak and peaks on adjacent cells are separated by a longitudinal cell separation distance and wherein the longitudinal cell separation distance between a first and a second cell is less than 0.08 millimeters, or between 0.04 and 0.08 millimeters.

Clause 44. The stent of clause 43, wherein the longitudinal cell separation distance is between 0.04 and 0.07 millimeters.

Clause 45. The stent of clause 43, wherein the longitudinal cell separation distance is between 0.04 and 0.06 millimeters.

Clause 46. The stent of any one of clauses 43-45, wherein every strut in the first cell is oriented parallel to the stent axis.

Clause 47. The stent of clause 46, wherein every strut in the second cell is oriented parallel to the stent axis.

Clause 48. The stent of any one of clauses 43-47, wherein the top bar further comprises a curved edge on a side opposite from the second end.

Clause 49. The stent of clause 48, wherein the top bar further comprises a first and a second top bar peak separated by the curved edge.

Clause 50. The stent of clause 49, wherein the first and second top bar peaks are each separated from peaks on an adjacent cell by the longitudinal separation distance Clause 51. The stent of any one of clauses 43-50, wherein each of the plurality of struts has a width to thickness ratio about equal to one.

Clause 52. The stent of any one of clauses 43-51, wherein each of the plurality of struts has a length to width ratio of between 15 and 19.

Clause 53. The stent of any one of clauses 43-52, wherein every adjacent peak on adjacent first and second cells are longitudinally aligned with each other or are laterally offset from longitudinal alignment between adjacent peaks less than 15 percent of a width of the narrowest strut.

Clause 54. The stent of any one of clauses 43-52, wherein every adjacent peak on adjacent first and second cells are longitudinally aligned with each other or are laterally offset from longitudinal alignment between adjacent peaks less than 10 percent of a width of the narrowest strut.

Clause 55. The stent of any one of clauses 42-54, wherein the stent has an expanded form, the expanded form having an expanded diameter, wherein the framework, in the expanded form, is biased toward the expanded diameter.

Clause 56. The stent of clause 55, wherein the expanded diameter is at least 4 millimeters.

Clause 57. The stent of clause 55, wherein the stent, in the expanded form, is compressible to a diameter of 1.35 millimeters.

Clause 58. The stent of any one of clauses 43-57, wherein the struts in the first cell are at least 10 percent wider than the struts in the second cell.

Clause 59. The stent of any one of clauses 43-58, wherein every strut in the first cell is oriented parallel to the stent axis.

Clause 60. The stent of any one of clauses 43-59, wherein every strut in the second cell is oriented parallel to the stent axis.

Clause 61. The stent of any one of clauses 42-60, wherein the stent is self-expanding.

Clause 62. The stent of any one of clauses 42-61, wherein the framework is constructed from super elastic nitinol.

LIST OF ELEMENTS 3. area
10. stent delivery system
11. catheter
13. catheter diameter
15. loading configuration
19. cell length
20. stent
21. framework
22. hollow cylindrical shape
23. length
24. stent axis
25. cell
26. discrete segment
27. adjacent pair of cells
28. peak
29. peak
30. strut
31. end
32. vertex
33. outer edge
34. width
35. width
36. thickness
38. rectangular cross section
39. width
40. T-bar
41. column
42. long axis
43. top bar
44. end
45. end
46. opposite ends
47. minimum width
48. slot
49. concave edge
51. first cell
52. second cell
53. lateral connection
54. end cell
55. flex cell
56. hoop cell
57. adjacent cells
58. eyelet
59. cell separation distance
60. loading diameter
61. tube diameter
62. expanded diameter
70. slot
71. slot
72. tall H shape
73. leg
74. bridge
80. adjacent pair of struts
81. rectangular space
82. width
85. continuous inner curve
86. radius
100. Coating layer
120. self expanding stent
158. rectangular eyelet
220. self expanding stent
258. alternate eyelet shape
C. tube circumference

What is claimed is:

1. A stent comprising:
a framework having a hollow cylindrical shape with a length along a stent axis, and the framework including a sequence of cells that each occupy a discrete segment of the stent length, and each of the cells including a plurality of struts with ends connected at respective vertices;
an adjacent pair of the cells being attached to one another by a first plurality of T-bars that each include a first column defining a long axis extending parallel to the stent axis and a top bar attached to one end of the first column, and an opposite end of the first column being attached to a first cell of the adjacent pair of cells, the top bar being attached at opposite ends to a second cell of the adjacent pair of cells, the top bar having a top bar edge that faces away from the first column and defines a first peak and a second peak separated by a concave curved edge portion;
a third cell of the sequence of cells, the third cell adjacent to the second cell opposite the first cell along the stent length, the third cell connected to the second cell by a second plurality of T-bars each having a top bar having a top bar edge defining a first peak and a second peak separated by a concave curved edge portion;
wherein the framework has a first total number of vertices on the first cell that face toward the second cell across a gap between the first cell and the second cell;
wherein the framework has a second total number of vertices on the second cell and first and second peaks of the second plurality of T-bars, combined, that face toward the first cell across the gap;
and wherein the first total number and the second total number are the same.

2. The stent of claim 1, wherein:
the concave curved edge portion straddles the long axis.

3. The stent of claim 2, wherein:
the sequence of cells includes at least one end cell, at least one flex cell, and at least one hoop cell; and
the adjacent pair of cells includes exactly one flex cell and exactly one hoop cell.

4. The stent of claim 2, wherein adjacent cells of the sequence of cells contact each other when the framework is in a loading configuration.

5. The stent of claim 2, wherein each of the vertices define a continuous inner curve with a radius that is less than one half of a width of the struts joined by a respective vertex of the vertices.

6. The stent of claim 1, wherein:
the hollow cylindrical shape is movable among a loading diameter that is smaller than a tube diameter which is smaller than an expanded diameter;
the framework is biased toward the expanded diameter; and
every strut of the first cell is oriented parallel to the stent axis when the hollow cylindrical shape is at the tube diameter.

7. The stent of claim 1, wherein:
the first column has a minimum width perpendicular to the long axis that is wider than a maximum width of each of the plurality of struts.

8. The stent of claim 1, wherein the framework is biased toward an expanded diameter.

9. The stent of claim 8, wherein the expanded diameter is four millimeters, or five millimeters, or six millimeters.

10. The stent of claim 1, wherein each cell of the adjacent pair of cells of the sequence of cells are on opposite sides of a plane oriented perpendicular to the stent axis when the hollow cylindrical shape is at a tube diameter.

11. The stent of claim 1, wherein each of the vertices define a peak and wherein peaks defined by vertices on the first and second cells are separated by a longitudinal cell separation distance of less than 0.08 millimeters when the hollow cylindrical shape is at a tube diameter.

12. The stent of claim 1, also comprising a coating on a surface of the framework, wherein the coating includes a therapeutic agent and a polymer matrix, and wherein the therapeutic agent is incorporated in the polymer matrix.

13. The stent of claim 12, wherein the therapeutic agent is a restenosis inhibiting agent, and wherein the restenosis inhibiting agent is paclitaxel, sirolimus, pimecrolimus, tacrolimus, everolimus, zotarolimus, novolimus, myolimus, temsirolimus, deforolimus, or biolimus.

14. The stent of claim 12, wherein the coating has a thickness in the range of 1 to 30 microns.

15. The stent of claim 14, wherein the struts each have a circumferential surface extending completely around a circumference of the strut, and wherein the coating covers the circumferential surface of each strut.

16. The stent of claim 15, wherein the struts each have a thickness in the range of 85 to 135 microns, and wherein for each strut the combined thickness of the coating and the strut is greater than the thickness of the strut but does not exceed 150 microns.

17. A method of loading a self-expanding stent into a catheter of a stent delivery system, comprising the steps of:
putting the stent of claim 1 in a loading configuration, which includes simultaneously compressing the self expanding stent circumferentially and longitudinally while sliding the stent into the catheter; and
moving adjacent cells of the self expanding stent from out of contact into contact responsive to the longitudinal compression.

18. The stent of claim 8, wherein the framework comprises superelastic nitinol.

19. A stent, comprising:
a self-expanding framework having a hollow cylindrical shape with a length along a stent axis, and the framework including a sequence of cells that each occupy a discrete segment of the stent length, and each of the cells including a plurality of struts with ends connected at respective vertices, the framework biased to an expanded diameter and compressible to a tube diameter smaller than the expanded diameter;
an adjacent pair of the cells being attached to one another by a plurality of T-bars that each include a column defining a long axis extending parallel to the stent axis and a top bar attached to one end of the column, and an opposite end of the column being attached to a first cell of the adjacent pair of cells, and the top bar being attached at opposite ends to a second cell of the adjacent pair of cells, the second cell defining a strut pair width across adjacent pairs of struts of the second cell with the framework at the tube diameter;
wherein the top bar has a top bar edge that faces away from the column and defines a first peak and a second peak separated by a concave curved edge portion; and
wherein each of the vertices defines a peak and wherein with the framework at the tube diameter oppositely facing peaks defined by vertices of the first and second cells face toward one another across a gap between the first and second cells and are longitudinally aligned with each other or are laterally offset by a distance that is less than 20 percent of the strut pair width defined by the second cell.

20. The stent of claim 19, wherein the framework is self-expanding.

21. The stent of claim 20, wherein the framework comprises superelastic nitinol.

22. The stent of claim 21, wherein each of the vertices define a peak and wherein peaks defined by vertices on the first and second cells are separated by a longitudinal cell separation distance of less than 0.08 millimeters when the hollow cylindrical shape is at the tube diameter.

23. A stent, comprising:
a framework having a hollow cylindrical shape with a length along a stent axis, the framework including a sequence of cells that each occupy a discrete segment of the length, the sequence of cells including first and second end cells and intermediate cells longitudinally between the first and second end cells, each of the cells of the sequence of cells including a plurality of struts with ends connected at respective vertices;
an adjacent pair of the intermediate cells being attached to one another by a first plurality of T-bars that each include a first column defining a long axis extending parallel to the stent axis and a top bar attached to one end of the first column, and an opposite end of the first column being attached to a first cell of the adjacent pair of the intermediate cells, the top bar being attached at opposite ends to a second cell of the adjacent pair of the intermediate cells, the top bar having a top bar edge that faces away from the first column and defines a first convex curved edge portion and a second convex curved edge portion separated by a concave curved edge portion;
wherein the hollow cylindrical shape is movable between a tube diameter and an expanded diameter greater than the tube diameter;
wherein the framework is biased to move the hollow cylindrical shape from the tube diameter to the expanded diameter;
wherein each of the vertices defines a peak; and
wherein peaks defined by vertices on the first cell face toward and are separated from peaks defined by vertices of the second cell by a longitudinal cell separation distance of less than 0.08 millimeters when the hollow cylindrical shape is at the tube diameter.

24. The stent of claim 23, also comprising:
a third cell of the intermediate cells, the third cell adjacent to the second cell opposite the first cell along the stent length, the third cell connected to the second cell by a second plurality of T-bars each having a top bar having a top bar edge defining first and second convex curved top bar edge portions, the first and second convex curved top bar edge portions separated by a concave curved top bar edge portion;
wherein the framework has a first total number of vertices on the first cell that face toward the second cell;
wherein the framework has a second total number of vertices on the second cell and first and second convex curved top bar edge portions of the second plurality of T-bars, combined, that face toward the first cell; and
wherein the first total number is equal to the second total number.

25. The stent of claim 24, wherein the framework comprises superelastic nitinol.

* * * * *